US012194293B2

United States Patent
Drake et al.

(10) Patent No.: US 12,194,293 B2
(45) Date of Patent: Jan. 14, 2025

(54) IMPLANTABLE MEDICAL LEAD

(71) Applicant: Medtronic, Inc., Minneapolis, MN (US)

(72) Inventors: Ronald A. Drake, St. Louis Park, MN (US); Mary M. Morris, Shoreview, MN (US); McKenna Rose Redmond Del Toro, Snohomish, WA (US); Megan L. Platner, Eden Prairie, MN (US); Kaileigh E. Rock, Saint Paul, MN (US); Brian P. Colin, Anoka, MN (US); William Eastman, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/378,486

(22) Filed: Jul. 16, 2021

(65) Prior Publication Data

US 2022/0023621 A1    Jan. 27, 2022

Related U.S. Application Data

(60) Provisional application No. 63/056,812, filed on Jul. 27, 2020.

(51) Int. Cl.
*A61N 1/05*    (2006.01)

(52) U.S. Cl.
CPC .................................. *A61N 1/0573* (2013.01)

(58) Field of Classification Search
CPC ................. A61N 1/0573; A61N 1/372; A61N 2001/058; A61B 2017/3488; A61M 29/00
See application file for complete search history.

(56) References Cited

U.S. PATENT DOCUMENTS

| | | | |
|---|---|---|---|
| 3,572,858 | A | 3/1971 | Pompei |
| 6,277,107 | B1 | 8/2001 | Lurie et al. |
| 6,662,045 | B2 | 12/2003 | Zheng et al. |
| 7,112,197 | B2 | 9/2006 | Hartley et al. |
| 7,628,801 | B2 | 12/2009 | Westlund et al. |
| 7,815,577 | B2 | 10/2010 | Krishnan |
| 7,983,765 | B1 | 7/2011 | Doan et al. |

(Continued)

FOREIGN PATENT DOCUMENTS

| | | |
|---|---|---|
| CN | 105193476 A | 12/2015 |
| WO | 02/058780 A1 | 8/2002 |

OTHER PUBLICATIONS

International Search Report and Written Opinion of International Application No. PCT/US2021/042288, mailed Oct. 25, 2021, 9 pp.

*Primary Examiner* — Scott Luan
(74) *Attorney, Agent, or Firm* — Shumaker & Sieffert, P.A.

(57) ABSTRACT

An implantable medical lead comprising a lead body defining a lumen. The lead body includes one or more tines substantially at a distal end of the lead body. An inner member extending within the lead body lumen is configured to rotate relative to the lead body and configured to cause a rotation of a dilator. The dilator is configured such that the rotation causes or enables a lateral translation of the dilator from a first position proximal to a lead body opening to a second position distal to the lead body opening. The implantable medical lead may include a probe wire configured to slidably translate through an inner lumen of the dilator.

20 Claims, 8 Drawing Sheets

(56) References Cited

U.S. PATENT DOCUMENTS

| | | | |
|---|---|---|---|
| 8,406,901 B2* | 3/2013 | Starkebaum | A61N 1/05 |
| | | | 607/130 |
| 8,634,932 B1 | 1/2014 | Ye et al. | |
| 9,855,421 B2 | 1/2018 | Garai et al. | |
| 10,368,911 B2* | 8/2019 | Davies | A61B 90/39 |
| 2004/0133113 A1 | 7/2004 | Krishnan | |
| 2005/0136385 A1 | 6/2005 | Mann et al. | |
| 2007/0156215 A1 | 7/2007 | Jensen et al. | |
| 2010/0204766 A1* | 8/2010 | Zdeblick | A61N 1/025 |
| | | | 607/119 |
| 2013/0184551 A1* | 7/2013 | Paganelli | A61B 17/02 |
| | | | 600/377 |
| 2013/0267885 A1* | 10/2013 | Celermajer | A61F 2/2412 |
| | | | 604/8 |
| 2018/0168687 A1* | 6/2018 | Drake | A61N 1/3756 |
| 2018/0333203 A1* | 11/2018 | Kellerman | A61M 25/0108 |
| 2020/0001070 A1 | 1/2020 | Eversull et al. | |
| 2020/0046407 A1 | 2/2020 | Drake et al. | |
| 2020/0094061 A1 | 3/2020 | Ghosh | |
| 2020/0114146 A1* | 4/2020 | Foster | A61N 1/0573 |
| 2020/0197693 A1* | 6/2020 | Liu | A61N 1/0573 |
| 2020/0261734 A1* | 8/2020 | Yang | A61N 1/0573 |
| 2021/0045773 A1* | 2/2021 | Kuhn | A61M 29/00 |
| 2022/0401722 A1* | 12/2022 | Seifert | A61N 1/057 |

* cited by examiner

IMPLANTABLE MEDICAL LEAD

This application claims the benefit of U.S. Provisional Patent Application Ser. No. 63/056,812 (filed Jul. 27, 2020), which is entitled, "IMPLANTABLE MEDICAL LEAD" and is incorporated by reference herein in its entirety.

TECHNICAL FIELD

This disclosure is related to medical devices such as implantable medical leads.

BACKGROUND

Various types of implantable medical leads have been implanted for treating or monitoring one or more conditions of a patient. Such implantable medical leads may be adapted to allow medical devices to monitor or treat conditions or functions relating to heart, muscle, nerve, brain, stomach, endocrine organs or other organs and their related functions. Implantable medical leads include electrodes and/or other elements for physiological sensing and/or therapy delivery. Implantable medical leads allow the sensing/therapy elements to be positioned at one or more target locations for those functions, while the medical devices electrically coupled to those elements via the leads are at different locations.

Implantable medical leads, e.g., distal portions of elongated implantable medical leads, may be implanted at target locations selected to detect a physiological condition of the patient and/or deliver one or more therapies. For example, implantable medical leads may be delivered to locations within an atria or ventricle to sense intrinsic cardiac signals and deliver pacing or antitachyarrhythmia shock therapy from a medical device coupled to the lead. In other examples, implantable medical leads may be tunneled to locations adjacent a spinal cord or other nerves for delivering pain therapy from a medical device coupled to the lead. Implantable medical leads may include anchoring components to secure a distal end of the lead at the target location.

SUMMARY

An implantable medical lead comprises a lead body comprising an interior surface with the interior surface defining a lumen. The lead body defines a longitudinal axis extending through the lumen. The lead includes an inner member within the lumen, with the inner member configured to rotate around the longitudinal axis and relative to the inner surface defining the lumen. A dilator including a dilator electrode is coupled to the inner member. The dilator is configured to rotate relative to the inner surface, and the inner member is configured to transmit a torque to the dilator when the inner member rotates around the longitudinal axis of the lead body. The dilator is configured to penetrate tissue when the dilator receives the torque and the dilator contacts the tissue. The implantable medical lead further includes a fixation member (e.g., one or more tines) configured to secure a distal end of the lead body to the tissue. In examples, the implantable medical lead comprises a probe wire configured to extend through an inner lumen and an inner lumen opening of the dilator.

In examples, the dilator defines a dilator axis and includes a helical screw thread on an exterior surface of the dilator, and the helical screw thread is configured to cause the dilator to translate substantially parallel to the dilator axis when the inner member transmits the torque to the dilator and the helical screw thread contacts a tissue in a patient, such as a heart tissue. The inner member may be configured to stretch when the dilator laterally translates within the tissue. In examples, the inner member includes a helical coil configured to stretch when the dilator laterally translates. The implantable lead may include a return electrode mounted to the lead body, and may include a distal electrode mounted distal to the return electrode. The dilator electrode, the distal electrode, and/or the return electrode may be coupled to respective electrical conductors that extend through the lead body, and thereby act as electrodes for sensing and/or therapy.

A technique for delivering a dilator electrode to a target site in a patient includes navigating a lead body to the target site. The technique includes contacting a fixation member (e.g., one or more tines) attached to a distal end of the lead body with tissues at or near the target site, and grasping the tissues using the one or more tines. The technique further includes rotating an inner member within a lumen defined by an interior surface of the lead body, with the rotation relative to the interior surface. The technique includes rotating the dilator including the dilator electrode using the rotation of the inner member, and translating the dilator into the tissues at or near the target site using the rotation of the dilator. The technique may include translating a probe wire through an inner lumen defined by the inner member and the dilator. The technique may include penetrating the tissues at or near the target site with the probe wire and using the probe wire to guide the translation of the dilator into the tissues.

The details of one or more examples are set forth in the accompanying drawings and the description below. Other features, objects, and advantages will be apparent from the description and drawings, and from the claims.

DETAILED DESCRIPTION

Figure 1:
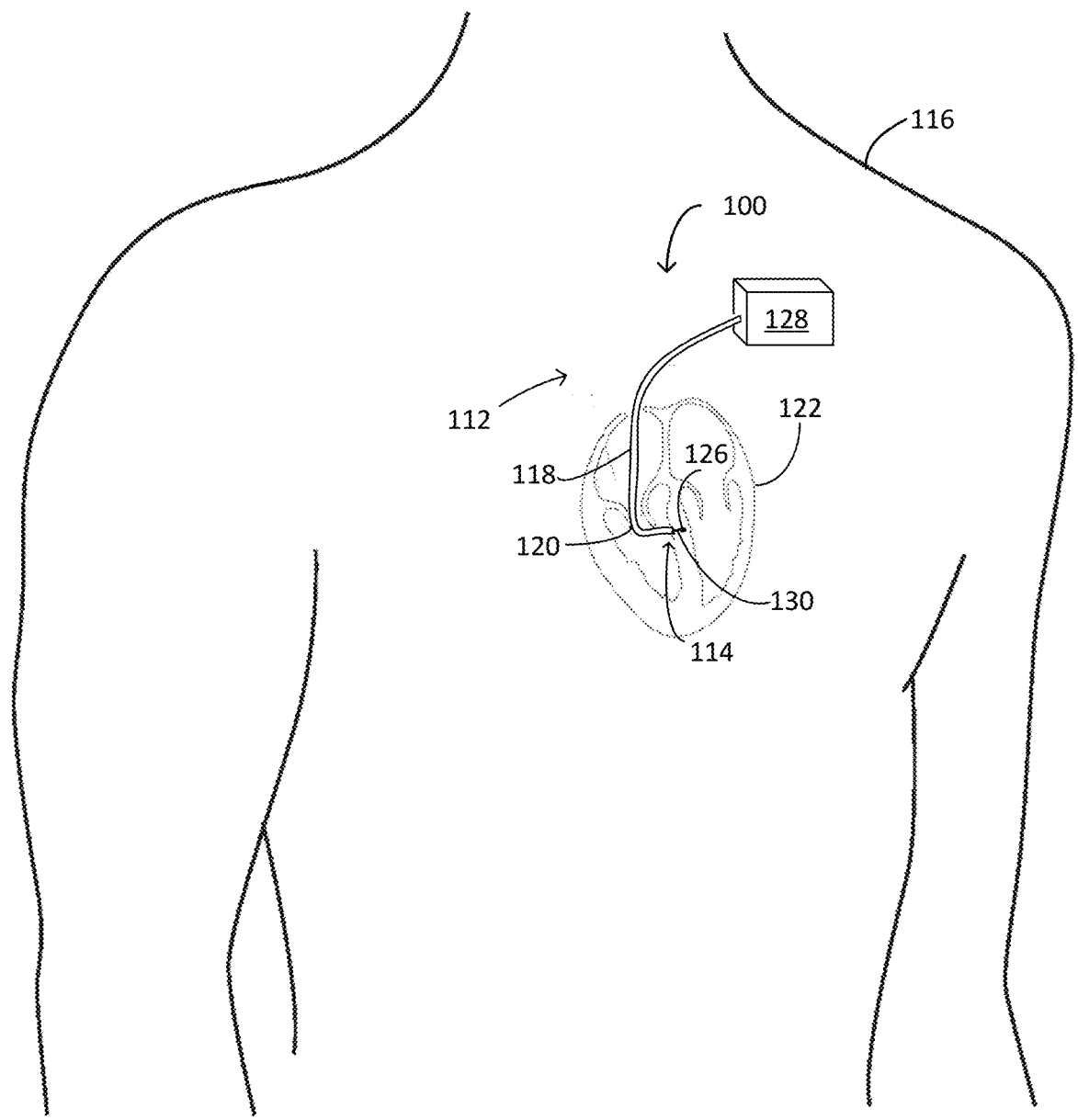
FIG. 1 is a conceptual diagram illustrating an example implantable medical lead implanted at an example target site.

This disclosure describes an implantable medical lead configured to deliver a dilator electrode to tissues at a target site within a patient. A dilator including the dilator electrode is configured to translate laterally and penetrate tissues at or near the target site, allowing for delivery of electrical stimulation therapies to the tissue. For example, the dilator may be configured to penetrate the septum of a patient's heart in order to deliver electrical stimulations to activate a left bundle branch (LBB), other conduction system tissues, and/or or other ventricular tissues of the heart. The dilator is configured to penetrate the tissues as a clinician causes the dilator to rotate about a dilator axis. The dilator may be configured such that control of the rotation controls a depth to which the dilator penetrates the tissues (e.g., ventricular tissues), allowing the dilator to be substantially positioned at a pre-determined location based on, for example, pace mapping. The implantable medical lead includes an inner member allowing a clinician to transmit a torque causing rotation of the dilator and providing for control of the penetration depth. In examples, the implantable medical lead includes a probe wire and a probe electrode configured to penetrate the tissues at or near the target site (e.g., prior to penetration by the dilator). The probe wire may be configured to conduct pace mapping within the tissue, and may be configured to serve as a guiding wire for the dilator during dilator rotation and penetration of the tissue.

The implantable medical lead includes an elongated lead body having an interior surface defining a lead body lumen and defining a lumen opening at a distal end of the lead body. The lead body includes a fixation member (e.g., one or more tines) configured to extend from the distal end of the lead body and implant within tissue, such that the distal end of the lead body may be substantially anchored within a tissue wall (e.g., a septal wall) at or near the target site. In examples, the distal end of the lead body is delivered to the tissue wall using a delivery catheter, and the tines are resiliently biased to expand radially outward as the lead body is distally displaced relative to the delivery catheter (e.g., the lead body is distally extended relative to the delivery catheter and/or the delivery catheter is proximally withdrawn relative to the lead body).

The lead body lumen is configured to surround the dilator, and configured such that the dilator may slidably translate through the lead body lumen and through the lumen opening. Further, the dilator is configured to be rotatable within the lead body lumen about the dilator axis. An exterior surface of the dilator is configured such that, when a distal end of the dilator is in contact with tissues at or near the target site, a rotation of the dilator may at least in part cause the dilator to penetrate and translate within the tissue. In examples, the dilator exterior surface defines a helical thread pattern around the dilator axis, with the helical thread pattern configured to engage the tissue and convert a rotation of the dilator around the dilator axis into a lateral translation substantially parallel to the dilator axis. The lateral translation of the dilator may cause the dilator to travel from a location at least partially within the lead body lumen, through the lumen opening at the distal end of the lead body, and into tissues at or near the target site. In some examples, when the one or more tines anchor the lead body distal end to a tissue wall (e.g., a septal wall), the dilator may be slidably translated toward the lead body distal end to cause contact between the tissue wall and a distal end of the dilator. In some examples, when the one or more tines anchor the lead body distal end to a tissue wall, the dilator may be positioned within the lead body lumen such that the distal end of the dilator is in contact with the tissue wall when the one or more tines anchor.

An inner member is attached to a proximal end of the dilator and additionally extends through the lead body lumen. At least some portion of the inner member (e.g., the portion attached to the proximal end of the dilator) is configured to pass through the lumen opening of the lead body lumen. The inner member is rotatable within the lead body lumen and configured to transmit a torque to the dilator, such that when the inner member rotates within the lead body lumen (e.g., is caused to rotate by a clinician), the inner member causes the dilator to rotate substantially synchronously with the inner member. The inner member may be a coil (e.g., a helical coil) configured to transfer the torque to the dilator. In addition, the inner member may be expandable lengthwise, such that a displacement between a first point on the inner member and a second point on the inner member increases when a distally directed force is exerted on a distal end of the inner member (e.g., exerted by the dilator during tissue penetration). Thus the inner member may stretch within the lead body lumen when the dilator penetrates and translates within the tissue. In examples, the lengthwise expansion of the inner member allows lead body to remain attached to the lead body as the dilator translates into the tissue.

The implantable medical lead may be configured to conduct pace mapping within the septum or other ventricular tissues (e.g., prior to dilator penetration) using a probe wire extending through the implantable medical lead. The probe wire may extend through a channel defined by the inner member and through an inner lumen of the dilator. The probe wire is slidably translatable within the channel and the inner lumen, and configured such that at least a portion of the probe wire may be extended from an inner lumen opening at a distal end of the dilator. The probe wire may penetrate the tissues and place a probe electrode (e.g., an uninsulated section of the probe wire) in contact with a tissue interior, such as the interior of a septal wall. In examples, the probe electrode is in electrical communication with processing circuitry configured to deliver electrical therapy and/or conduct electrical sensing via the probe electrode. A clinician may manipulate the slidably translatable probe wire to vary a depth of the probe electrode in the tissue (e.g., in a septal wall) in order to conduct pace mapping with limited distortion of the target tissue area.

In examples, a distal portion of the probe wire includes a shape memory alloy configured to define a curvature of the probe wire when the distal portion is unconstrained by surrounding tissue. For example, the shape memory alloy may be configured to define a curvature when the distal portion of the probe wire has passed from a right ventricle of heart through the septum and entered the left ventricle. The distal portion of the probe may be resiliently biased to form a relatively compact configuration, such that a straight-line displacement between two points on the distal portion is less than a displacement measured along the probe wire itself. For example, the distal portion of the probe wire may be configured to form a loop (e.g., helix) or some other shape. The relatively compact configuration may serve to substantially retain the distal end of the probe wire nearer to the septal wall (e.g., in the left ventricle), as well as serve as a fluoroscopy marker for the septal wall (e.g., the endocardial surface of the septal wall).

FIG. 1 is a conceptual diagram illustrating a portion of an example medical device system 100 including an implantable medical lead 112. Implantable medical lead 112 includes an elongated lead body 118 with a distal portion 120 positioned at a target site 114 within a patient 116. Distal portion 120 may be, for example, a sleeve head of implantable medical lead 112. In some examples, as illustrated in FIG. 1, the target site 114 may include a portion of a heart 122, such as an interventricular septal wall of a right ventricle (RV) of heart 122, as illustrated in FIG. 1, or atrioventricular septal wall of a right atrium (RA) of heart 122 or other locations within a body of patient 116. A clinician may maneuver distal portion 120 through the vasculature of patient 116 in order to position distal portion 120 at or near target site 114. For example, the clinician may guide distal portion 120 through the superior vena cava (SVC), into the RA, and past the Tricuspid valve into the RV in order to access target site 114 on the atrioventricular septal wall. In some examples, other pathways or techniques may be used to guide distal portion 120 into other target implant sites within the body of patient 116. Medical device system 100 may include a delivery catheter and/or outer member (not shown), and implantable medical lead 112 may be guided and/or maneuvered within a lumen of the delivery catheter in order to approach target site 114. For example, in one or more examples described herein, target site 114 may be the triangle of Koch region in the atrioventricular septal wall of the patient's heart or the ventricular septal wall in the basal (e.g., high basal or high septal) region or apical (e.g., low septal or near the apex) region. Implantable medical lead 112 includes one or more tines (not shown) configured to grasp tissues at or near target site 114 and substantially secure a distal end of implantable medical lead 112 to the target site. For example, the one or more tines may be configured to substantially secure the distal end of implantable medical lead 112 to tissues of the interventricular septal wall of a right ventricle (RV) of heart 122.

Implantable medical lead 118 includes a dilator 126 including a dilator electrode. Dilator 126 is configured to penetrate the tissues at or near target site 114. For example, dilator 126 may be configured to penetrate the atrioventricular septal wall of a right ventricle (RV) of heart 122 in order to stimulate the LBB of heart 122 using the dilator electrode. The dilator electrode of dilator 126 may be electrically connected to a conductor (not shown) extending through implantable medical lead 112 from the dilator electrode. In examples, the conductor is electrically connected to therapy delivery circuitry of an implantable medical device (IMD) 128, with the therapy delivery circuitry configured to provide electrical signals through the conductor to the dilator electrode of dilator 126. The dilator electrode may conduct the electrical signals to the target tissue of heart 122, causing the cardiac muscle, e.g., of the ventricles, to depolarize and, in turn, contract at a regular interval. In examples in which dilator 126 penetrates to a position at or near the HB, RBB, LBB, or other specialized conductive tissue of heart 122, the cardiac pacing delivered via the dilator electrode may be conduction system pacing (CSP) of heart 122, which may provide more physiologic activation and contraction of heart 122. Dilator 126 may also be connected to sensing circuitry of IMD 128 via the conductor, and the sensing circuitry may sense electrical activity of heart 122 via dilator 126 (e.g., via the dilator electrode).

In some examples, dilator 126 is configured to be rotatable using inner member 130, and dilator 126 is configured to penetrate the tissues as the rotation occurs. For example, dilator 126 may define a helical screw thread configured to engage tissues at or near target site 114 and convert a rotation of dilator 126 into a lateral translation of dilator 126 into the tissue. The rotation of inner member 130 and dilator 126 may be controlled by a clinician, such that dilator 126 may be positioned relatively precisely within the atrioventricular septal wall. For example, a clinician may control the rotation of inner member 130 and dilator 126 by rotating a connector pin on the proximal end of lead body 118. In some examples, a proximal end of inner member 130 is configured to substantially maintain electrical contact with processing circuitry as inner member 130 is rotated. For example, a proximal end of inner member 130 may have an uninsulated section configured to establish electrical contact with a component (e.g., an alligator clip) electrically connected to the processing circuitry. The uninsulated section may be configured to maintain the electrical contact with the component (e.g., the alligator clip) as inner member 130 is rotated. This may rotation of inner member 130 without an attendant requirement to electrically disconnect and/or reconnect inner member 130 to the processing circuitry.

As will be discussed, in some examples, dilator 126 and inner member 130 may be guided to target site 114 using a probe wire (not shown) configured to penetrate the tissues at or near target site 114. The probe wire may include a probe electrode connected to processing circuitry configured to sense a condition using the probe electrode as probe wire penetrates the tissues. For example, the probe wire may be connected to processing circuitry configured to electrically map within the interventricular septal wall in order to locate advantageous positions for conduction system pacing using the LBB.

Figure 2:
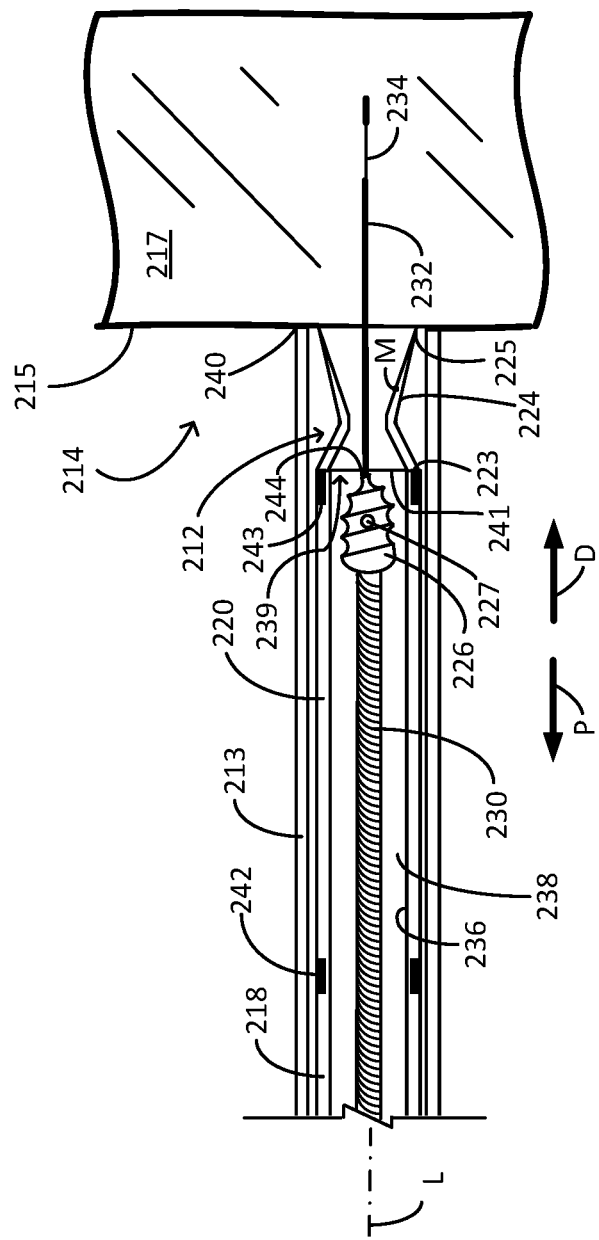
FIG. 2 is a plan view with selected cross-sections illustrating an example implantable medical lead.
Figure 3:
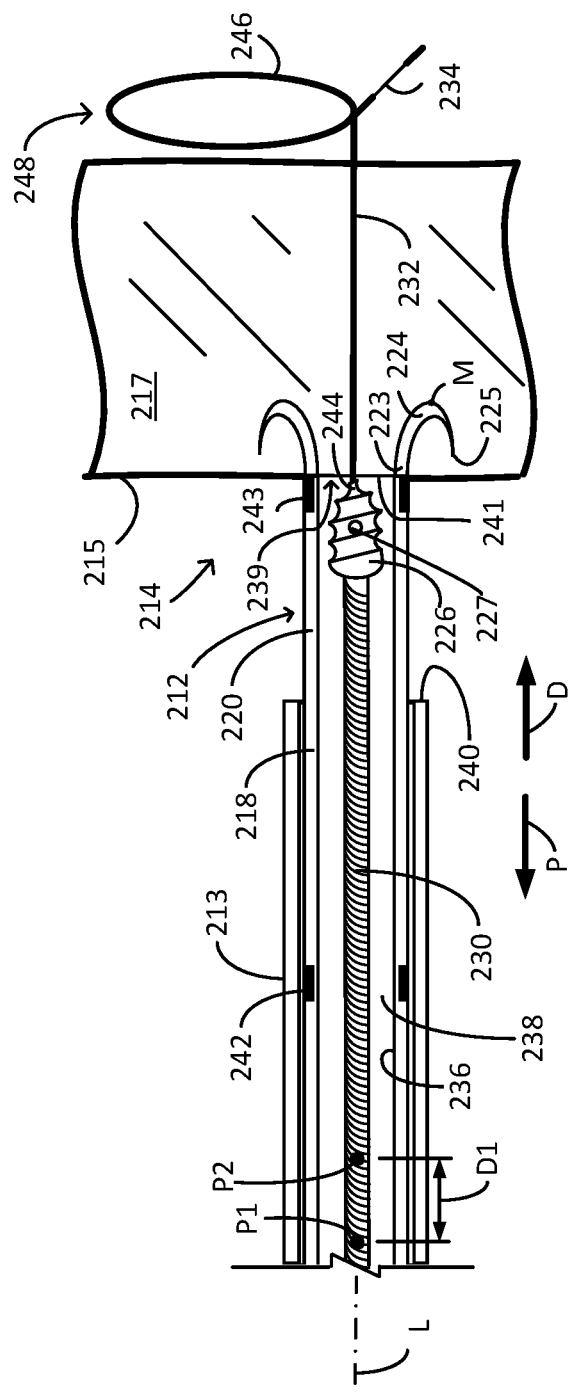
FIG. 3 is a plan view with selected cross-sections illustrating the implantable medical lead of FIG. 2 in a second configuration.
Figure 4:
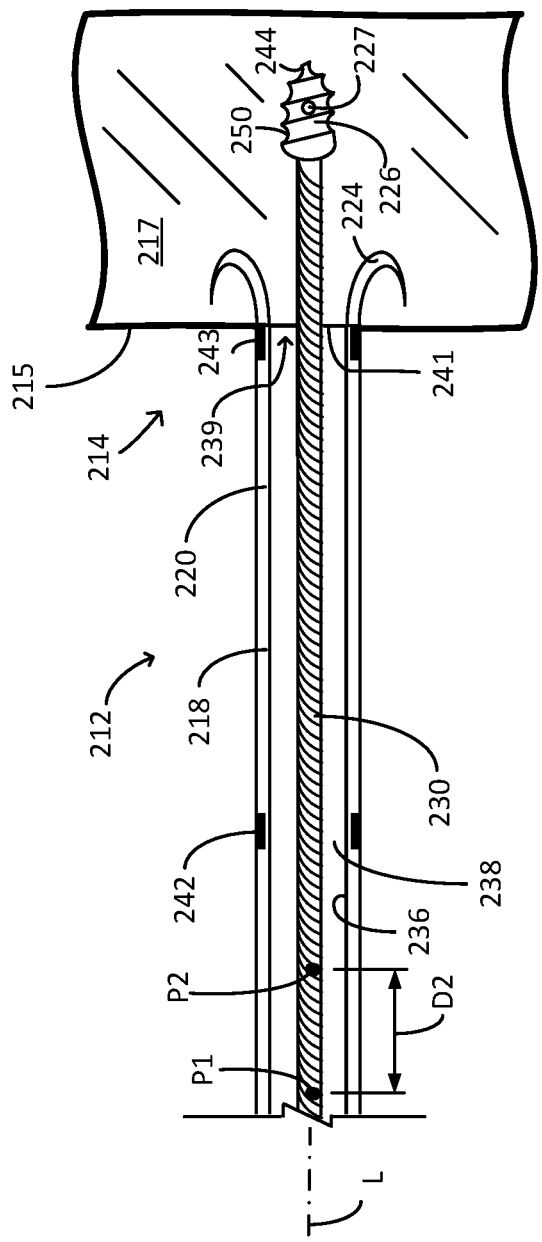
FIG. 4 is a plan view with selected cross-sections illustrating the implantable medical lead of FIG. 1 and FIG. 2 in a third configuration.

FIGS. 2, 3, and 4 are conceptual diagrams illustrating a plan view of a portion of an implantable medical lead 212 in various operating configurations. Implantable medical lead 212 is an example of implantable medical lead 112 (FIG. 1). FIGS. 2, 3, and 4 depict implantable medical lead 212 in the proximity of a target site 214 on a tissue wall 215 of tissue 217. Tissue wall 215 may be, for example, the interventricular septal wall of a right ventricle (RV) of heart 122, and tissue 217 may be the septum of heart 122 (FIG. 1). Implantable medical lead 212 includes lead body 218, distal portion 220 of lead body 218 ("lead body distal portion 220"), dilator 226, and inner member 230, which may be configured similarly to and operate relative to other implantable medical lead 212 components in the same manner as the like-named components of implantable medical lead 112. Further, although FIGS. 2 and 3 depict implantable medical lead 212 within a lumen of a delivery catheter 213 for the purpose of discussing various operating modes of implantable medical lead 212, implantable medical lead 212 may operate in either the absence or the presence of delivery catheter 213. FIGS. 2, 3, and 4 illustrate a longitudinal cross-section of lead body 218 and delivery catheter 213, with a cutting plane taken parallel to the page.

FIG. 2 depicts implantable medical lead 212 including lead body 218 positioned within a lumen of delivery catheter 213. Lead body 218 comprises an interior surface 236 ("lead interior surface 236") surrounding a longitudinal axis L defined by lead body 218. Lead interior surface 236 defines a lumen 238 ("lead body lumen 238"), and defines an opening 239 to lead body lumen 238 ("lumen opening 239") at a distal end 241 of lead body 218 ("lead distal end 241"). Implantable medical lead 212 includes dilator 226 positioned within lead body lumen 238, and inner member 230 extending through lead body lumen 238. Inner member 230 and dilator 226 are configured to rotate within lumen 238 relative to interior surface 236. Additionally, inner member 230 is configured to transmit a torque to dilator 226, such that when inner member 230 rotates substantially around a longitudinal axis L defined by lead body 218, inner member 230 causes a rotation of dilator 226 around longitudinal axis L.

In general, a tine may refer to any structure that is capable of securing a lead or leadless implantable medical device to a location within the heart. In some examples, a tine may be composed of a shape-memory allow that allows deformation along the length of the tine. A tine may be substantially flat along the length of the tine.

One or more tines such as tine 224 extend distally from lead body 218 around lumen opening 239. In general, a tine may refer to any structure that is capable of securing a lead or leadless implantable medical device to a tissue at a target site (e.g., target site 114 (FIG. 1)) within a patient. In some examples, a tine may be composed of a shape-memory that allows deformation along the length of the tine. A tine may be substantially flat along the length of the tine. Tine 224 includes a fixed end 223 coupled to lead body 218 and a free end 225 opposite fixed end 223. In the configuration depicted in FIG. 2, tine 224 is depicted in a delivery configuration, wherein free end 225 is distal to a midpoint M on tine 224 between fixed end 223 and free end 225. Additionally, although FIG. 2 depicts implantable medical lead 212 (e.g., free end 225 of tine 224) in close proximity to a distal end 240 of delivery catheter 213 ("delivery catheter distal end 240"), implantable medical lead 212 is slidably translatable within delivery catheter 213 and may be located anywhere in delivery catheter 213 relative to delivery catheter distal end 240.

A probe wire 232 including a probe electrode 234 extends substantially parallel to longitudinal axis L through an inner channel (not illustrated) of inner member 230 and an inner lumen (not illustrated) defined by dilator 226. Probe wire 232 extends through an inner lumen opening substantially at a distal end 244 of dilator 226 ("dilator distal end 244"). Probe wire 232 is slidably translatable within the inner channel of inner member 230, within the inner lumen of dilator 226, and through the inner lumen opening, such that probe wire 232 may be manipulated to move both distally and proximally relative to, for example, dilator 226 and/or interior surface 236. Probe wire 232 is configured to penetrate tissue wall 215 and establish probe electrode 234 within tissue 217. Probe electrode 234 may be in electrical communication with processing circuitry configured to deliver electrical therapy and/or conduct electrical sensing via probe electrode 234. Thus, with implantable medical lead 212 positioned proximal to delivery catheter distal end 240, a clinician may manipulate the slidably translatable probe wire 232 to position probe electrode 234 to various depths within tissue 217 and utilize the processing circuitry to conduct pace mapping within tissue 217. For example, probe wire 232 may be placed at various depths across a septum of a heart in order to determine an advantageous location for stimulation of an LBB for conduction system pacing (CSP) of the heart. In examples, probe wire 232 is a relatively small diameter wire configured to penetrate and be repositioned with reduced (or minimal) trauma to the tissue 217. Probe wire 232 may be a memory shape alloy configured to substantially straighten when probe wire 232 is pulled proximally through tissue 217.

In examples, probe wire 232 includes a conductor substantially covered by an insulating jacket, and probe electrode 234 is a section of the conductor without the insulating jacket (e.g., with the insulating jacket removed). Other electrode configurations may be used in other examples. Implantable medical lead 212 further includes a return electrode 242 on lead body 218. In some examples, implantable medical lead 212 includes a distal electrode 243 positioned adjacent to or near lead distal end 241.

FIG. 3 illustrates a distal portion 246 of probe wire 232 ("probe distal portion 246") advanced completely through tissue 217 and forming a loop 248. FIG. 3 additionally depicts lead distal end 241 adjacent tissue wall 215 and tine 224 penetrating tissue wall 215, however medical lead 212 is configured such that probe wire 232 may be advanced through tissue 217 and form loop 248 with lead distal end 241 and tine 224 remaining substantially in the positions depicted in FIG. 2.

In examples, probe distal portion 246 includes a shape-memory alloy configured to define a curvature (e.g., loop 248) when probe distal portion 246 is unconstrained by surrounding tissues. For example, probe distal portion 246 may be configured to define the curvature of loop 248 when probe distal portion 246 is within a cardiac chamber of heart 122 (FIG. 1), such as a left atrium, left ventricle, right atrium, or right ventricle. Probe distal portion 246 may be configured to assume the relaxed, zero-stress condition when probe distal portion 246 is in a substantially zero-stress position, where any stresses on probe distal portion 246 arise from properties or phenomena purely internal to probe distal portion 246, such as mass, internal temperature, residual stresses, and the like. In examples, probe distal portion 246 may be imaged using fluoroscopy or other imaging techniques, such that loop 248 may serve as a visible marker. For example, loop 248 may serve as a visible marker indicating an approximate location of an endocardial surface of an interventricular septal wall of a left ventricle (LV) of heart 122.

As discussed, FIG. 3 depicts lead distal end 241 substantially adjacent tissue wall 215 and tine 224 having penetrated tissue wall 215. Tine 224 is configured to penetrate tissues when lead body 218 is translated proximally toward tissue wall 215. In examples, tine 224 is resiliently biased such that, unless sufficiently constrained (e.g., by delivery catheter 213) to maintain the delivery configuration depicted in FIG. 2, free end 225 tends to expand radially outward from longitudinal axis L to assume a delivery configuration. Tine 224 may be resiliently biased to cause free end 225 to pivot radially outward. For example, FIG. 3 depicts delivery catheter 213 withdrawn proximally such that delivery catheter distal end 240 is proximal to at least free end 225 of tine 224, such that tine 224 is relatively unconstrained. In an example, tine 224 establishes a first radial distance from free end 225 to longitudinal axis L in the delivery configuration and a second radial distance from free end 225 to longitudinal axis L in the deployment configuration, and the second radial distance is greater than the first radial distance. In some examples, free end 225 is proximal to midpoint M in the deployed configuration (e.g., tine 224 forms a U-shape in the deployed configuration).

FIG. 3 additionally depicts dilator 226 positioned within lead body lumen 238 and substantially adjacent tissue wall 215. Dilator 226 is in a first position proximal to lead distal end 241. As previously discussed, dilator 226 is rotatable within lead body lumen 238 and configured to axially translate (e.g., substantially parallel to longitudinal axis L) within lead body lumen 238. Inner member 230 is configured to transmit a torque to dilator 226 and cause a rotation of dilator 226 about longitudinal axis L. Dilator 226 is configured such that rotation of dilator 226 may cause the dilator to penetrate tissue wall 215 and translate within tissue 217. Loop 248 of probe wire 232 may be utilized as a fluoroscopy marker during the penetration of dilator 226 to assist in the placement of dilator 226 and dilator electrode 227 within tissue 217. For example, loop 248 may substantially mark a location of the LV endocardium as dilator 226 is rotated by inner member 230 for penetration of an interventricular septal wall. Loop 248 may act to stabilize probe wire 232 within tissue 217 to assist dilator 226 in traveling into tissue 217.

FIG. 4 illustrates dilator 226 having penetrated tissue wall 215 and within tissue 217 as a result of rotation about the longitudinal axis L by inner member 230. Delivery catheter 213 and probe wire 232 (FIGS. 2, 3) have been withdrawn proximally, although this is not necessary in all examples. Rotation of dilator 226 by inner member 230 has caused dilator 226 to translate from the first position proximal to lead distal end 241 (FIG. 2) to a second position distal to lead distal end 241. In the second position distal to lead distal end 241, dilator electrode 227 is in contact with tissues 217. In an example, dilator 226 is positioned distal to lead distal end 241 such that dilator electrode 227 is substantially located at a position within tissue 217 identified by probe electrode 234. Implantable medical lead 112 may be configured to allow dilator 226 to penetrate a septum of heart 122 (FIG. 1) to a depth such that dilator electrode 227 may stimulate the LBB of heart 122. Implantable medical lead 112 may be configured to allow dilator 226 to penetrate to a depth substantially determined by probe wire 232 during, for example, pace mapping of a septum or other ventricular tissues.

In some examples, dilator electrode 227 is mounted on an exterior surface 250 of dilator 226 ("dilator exterior surface 250") and is a substantially separate component from dilator exterior surface 250. In some examples, dilator electrode 227 comprises some or all of dilator exterior surface 250. In some examples, some or all of exterior surface 250 is an electrically conductive material substantially covered by an insulative material, with dilator electrode 227 defined by one or more portions of dilator exterior surface 250 where the insulative material is removed (e.g., a masked electrode). The insulative material may be is selectively removed at one or more locations to define dilator electrode 227 at a specific location on dilator 226, and/or to define a pattern of locations through which dilator electrode 227 may act.

Dilator exterior surface 250 may be configured such that, when dilator distal end 244 is in contact with tissue wall 215 and/or tissue 217, rotation of dilator 226 causes dilator 226 to penetrate tissue wall 215 and/or tissue 217. In examples, dilator exterior surface 250 is configured to engage with a surrounding environment (e.g., tissue 217) and convert a rotation of dilator 226 around longitudinal axis L into a translation of dilator 226 substantially parallel to longitudinal axis L. For example, dilator exterior surface 250 may define a helical thread pattern configured to engage tissue wall 215 and/or tissue 217 and convert a rotation of the dilator around a dilator axis defined by dilator 226 into a lateral translation substantially parallel to the dilator axis.

Inner member 230 may be configured to expand lengthwise (e.g., along longitudinal axis L) as inner member 230 transmits a torque to dilator 226 and dilator 226 translates within tissue 217. For example, inner member 230 may have a first configuration where a first point P1 on inner member 230 is displaced from a second point P2 by a displacement D1 (FIG. 3), and have a second configuration where the first point P1 is displaced from the second point P2 by a displacement D2 (FIG. 4), where D2 is greater than D1. Inner member 230 may be configured to substantially transition from the first configuration to the second configuration as dilator 226 translates substantially parallel to longitudinal axis L due to a rotation by inner member 230. Thus, some portion of or substantially all of inner member 230 may stretch within lead body lumen 238 when dilator 226 penetrates and translates within tissue 217. In an example, inner member 230 includes a helical coil around longitudinal axis L and configured to stretch while transferring a torque to dilator 226.

Lead body 218 may be configured such that distal electrode 243 is adjacent to or located on lead distal end 241. Lead body 218 may be configured such that distal electrode 243 is adjacent to or in contact with a tissue wall when lead distal end 241 is in contact with the tissue wall and/or the one or more tines (e.g., tine 224) penetrate the tissue wall. Distal electrode 243 may be in electrical communication with processing circuitry configured to deliver electrical therapy and/or conduct electrical sensing via distal electrode 243. For example, distal electrode 243 may contact the RV endocardium of a heart 122 (FIG. 1) when tine 224 when lead distal end 241 is in contact with the RV endocardium and/or tine 224 penetrates the RV endocardium. Distal electrode 243 may be configured to stimulate an interventricular septum of heart 122. Thus, implantable medical lead 112 may be configured such that dilator 226 and dilator electrode 227 may penetrate an interventricular septum to a depth sufficient to stimulate the LBB of heart 122 while distal electrode 243 is positioned adjacent or on the RV endocardium for stimulation of the RBB or right ventricular septum of heart 122.

Figure 5:
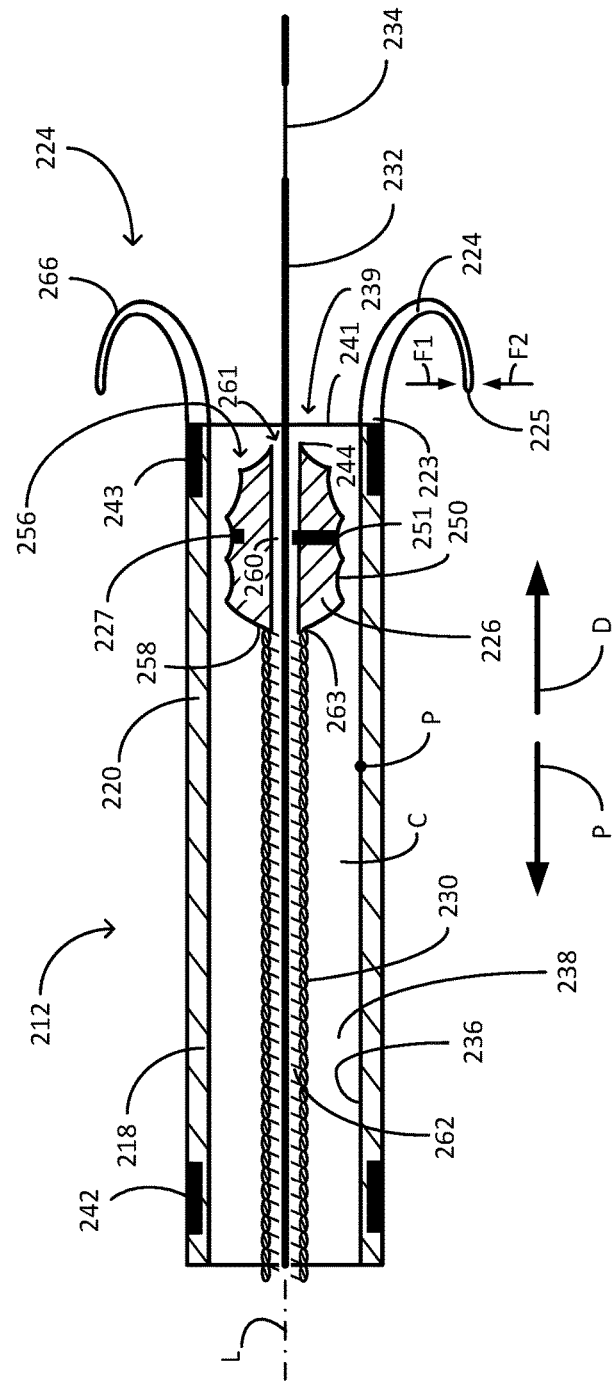
FIG. 5 is a plan view with selected cross-sections illustrating an another example implantable medical lead.

FIG. 5 illustrates an implantable medical lead 212 illustrating lead body 218, dilator 226, and inner member 230 in cross-section, with a cutting plane taken parallel to the page. FIG. 5 illustrates lead body 218, lead body distal portion 220, fixed end 223 and free end 225 of tine 224, dilator 226, dilator electrode 227, inner member 230, probe wire 232, probe electrode 234, lead interior surface 236, lead body lumen 238, lumen opening 239 at lead distal end 241, return electrode 242, distal electrode 243, and dilator distal end 244.

Dilator 226 is configured to rotate relative to lead interior surface 236. Dilator 226 is rotationally coupled to inner member 230, such that a rotation of inner member 230 around longitudinal axis L causes a rotation of dilator 226 around longitudinal axis L. In examples, inner member 230 is rotationally coupled to dilator 226 such that, when inner member 230 rotates about longitudinal axis L, dilator 226 rotates synchronously with inner member 230 about longitudinal axis L. Dilator 226 is configured to receive a torque imparted by inner member 230 and rotate (e.g., around longitudinal axis L) in response to the imparted torque. Dilator 226 may be configured to rotate substantially synchronously with inner member 230. In examples, dilator 226 is configured to translate in a direction substantially parallel to longitudinal axis L when inner member 230 rotates dilator 226.

Here and elsewhere, when a first component is rotationally coupled to a second component, this means a rotation of the first component causes a rotation of the second component. In examples, the rotation of the first component around an axis causes the rotation of the second component around the axis. The rotation of the first component in a particular direction (e.g., clockwise) around the axis may cause the rotation of the second component in the particular direction around the axis. In examples, the rotation of the first component causes the second component to rotate substantially synchronously with the first component.

Dilator 226 may be configured to convert a rotation (e.g., caused by inner member 230) into a lateral translation relative to interior surface 236, with the lateral translation substantially parallel to longitudinal axis L. Dilator 226 may convert the rotation into a lateral translation in the distal direction D. In examples, dilator 226 is configured such that rotation of dilator 226 in a first direction (e.g., clockwise) around longitudinal axis L generates a lateral translation of dilator 226 in a first lateral direction (e.g., the distal direction D), and a rotation of dilator 226 in a second direction (e.g., counter-clockwise) opposite the first direction generates a lateral translation of dilator 226 in a second lateral direction (e.g., the proximal direction P). In examples, dilator 226 includes a set of helical threads configured to engage a material surrounding dilator 226 (e.g., tissue 217 (FIGS. 2, 3, 4)) and convert the rotation of dilator 226 into the lateral translation of dilator 226.

Figure 6:
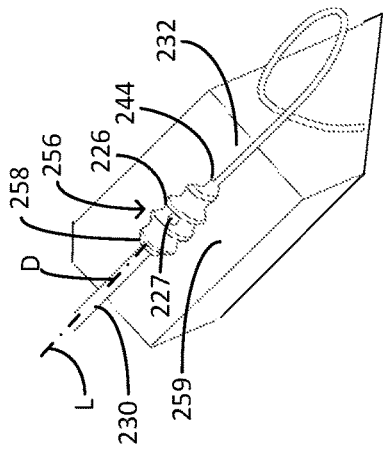
FIG. 6 is a perspective view illustrating a dilator and an inner member.

For example, FIG. 6 illustrates dilator 226 including helical threads 256. Dilator 226 defines a dilator axis D passing through dilator distal end 244 and a proximal end of dilator proximal 258 ("dilator proximal end 258"). Dilator axis D may be substantially parallel to longitudinal axis L. Dilator 226 is configured such that helical threads 256 substantially surround dilator axis D. Helical threads 256 are configured such that, when helical threads 256 engage surrounding material 259, helical threads 256 convert a rotation of dilator 226 about dilator axis D into a lateral translation of dilator 226 through material 259 in a direction substantially parallel to dilator axis D. Dilator 226 may be caused to rotate by a rotation of inner member 230. Helical threads 256 define a screw thread lead which substantially determines the lateral translation of dilator 226 (e.g., the thread advance) that occurs due to a given amount of rotation of inner member 230 around longitudinal axis L. Hence, rotation of inner member 230 may be used to control the lateral translation of dilator 226 within surrounding material 259. FIG. 6 further illustrates dilator electrode 227 and probe wire 232 forming a loop (e.g., loop 248 (FIG. 3)).

Helical threads 256 may be any type of thread capable of engaging surrounding material 259. Helical threads 256 may have any pitch, thread angle, major diameter, and root diameter. Helical threads 256 may be configured as V threads, square threads, acme threads, buttress threads, right-handed threads, left-handed threads, and other configurations. Dilator exterior surface 250 may define helical threads 256. In examples, helical threads 256 have a unitary body construction with dilator exterior surface 250, such that helical threads 256 and dilator exterior surface 250 are inseparable portions of dilator 226. In some examples, helical threads 256 comprise a separate thread insert or other component installed around some portion of dilator 226.

Figure 8:
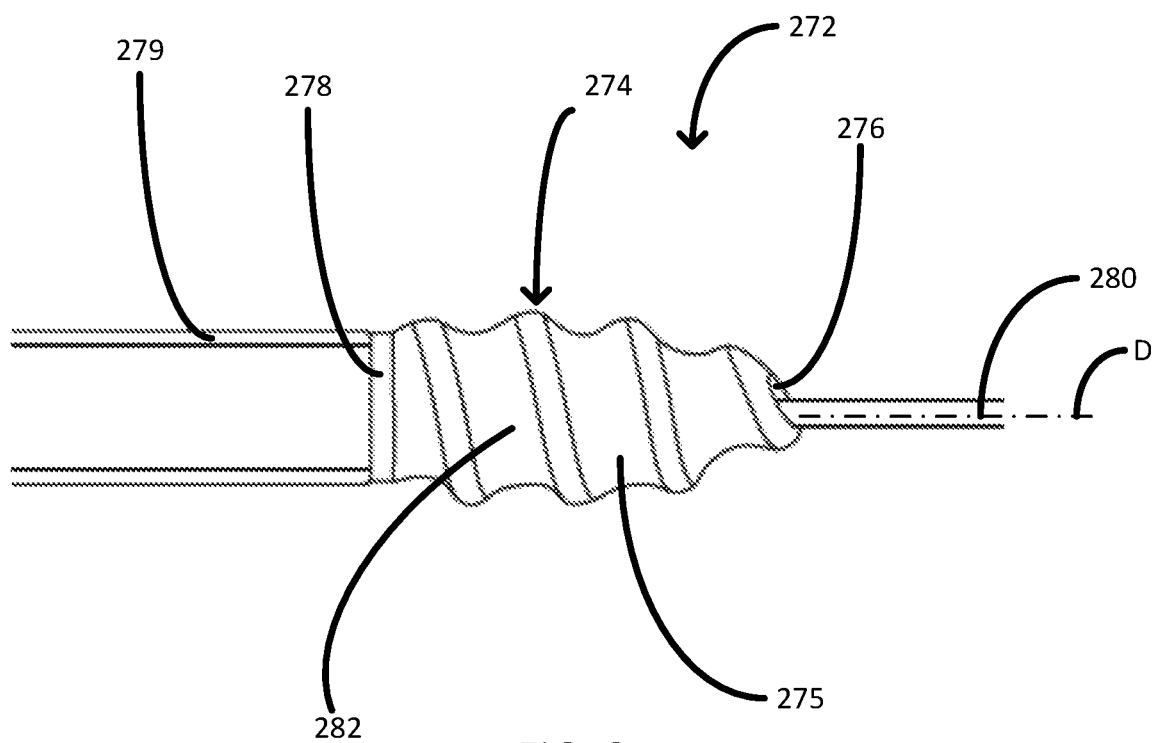
FIG. 8 is a perspective view illustrating a dilator and an inner member having helical threads.

FIG. 8 illustrates an example dilator 272 including helical threads 274 defined by a dilator exterior surface 275. Dilator 272 is an example of dilator 126, 226. Helical threads 274 extend around a dilator axis D substantially from dilator distal end 276 to dilator proximal end 278. An inner member 279 is mechanically attached to dilator proximal end 278. Inner member 279 is configured to transmit a torque around dilator axis D to dilator 272. A probe wire 280 extends through an inner lumen (not shown) of dilator 272. In the example of FIG. 8, dilator exterior surface 275 comprises an electrically conducting material and substantially defines dilator electrode 282 as a part of or substantially all of dilator exterior surface 275. For example, dilator exterior surface 275 may be substantially covered by an insulative material, with dilator electrode 282 defined by a portion of dilator exterior surface 275 where the insulative material is removed. As discussed, in other examples, dilator electrode 282 may be mounted on dilator exterior surface 275 as a substantially separate component from dilator exterior surface 275.

Figure 9:
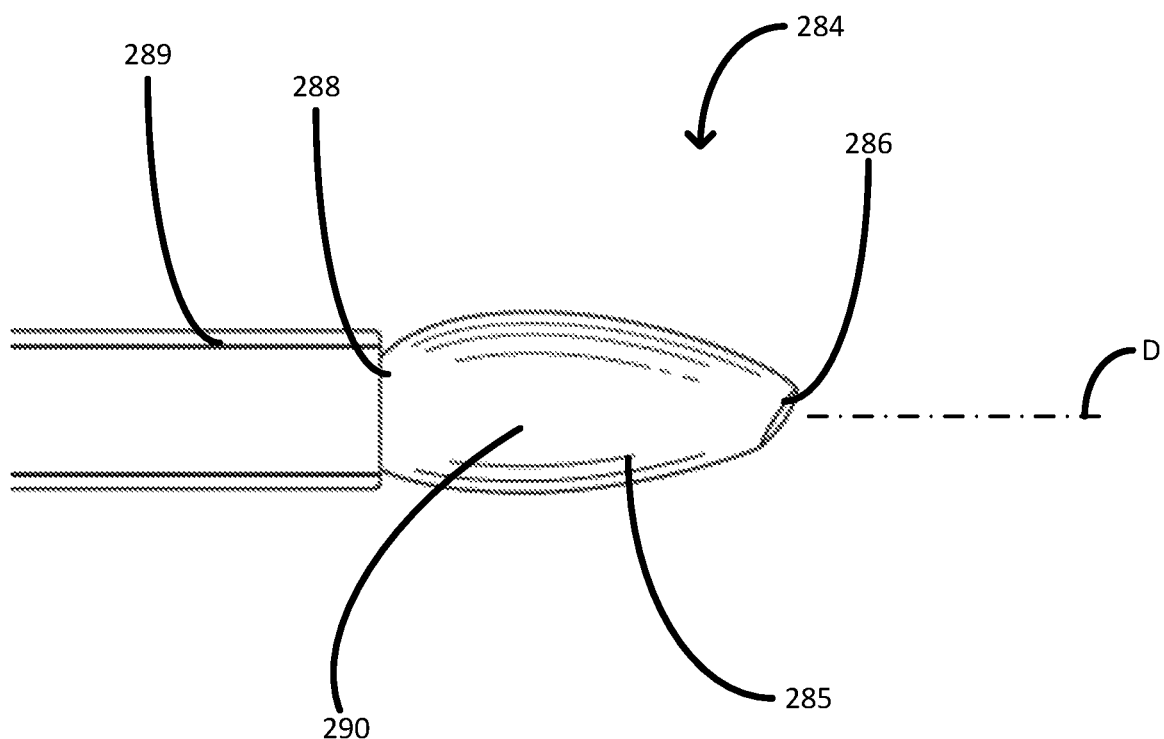
FIG. 9 is a perspective view illustrating a dilator defining a prolate spheroid.

FIG. 9 illustrates an example dilator 284 having dilator exterior surface 285. Dilator 284 is an example of dilator 126, 226. Dilator exterior surface 285 is configured to define a prolate spheroid shape substantially around dilator axis D. The prolate spheroid shape may extend substantially from dilator distal end 286 to dilator proximal end 288. In some examples, dilator distal end 286 may be configured to facilitate penetration of dilator 284 into tissue when dilator 284 rotates (e.g., rotates clockwise, counter-clockwise, and/or alternately clockwise and counter-clockwise). For example, dilator distal end 286 may include a bevel configured to facilitate the penetration. An inner member 289 is mechanically attached to dilator proximal end 288, with inner member 289 configured to transmit a torque around dilator axis D to dilator 284. The prolate spheroid shape of dilator 284 is configured to at least enable a translation of dilator 284 in a direction substantially parallel to dilator axis D when inner member 289 causes a rotation of dilator 284 around dilator axis D. Dilator exterior surface 285 may comprise an electrically conducting material and substantially define a dilator electrode 290 as a part of or substantially all of dilator exterior surface 285. In examples, dilator exterior surface may be substantially covered by an insulative material, with dilator electrode 290 defined by a portion of dilator exterior surface where the insulative material is removed. In other examples, dilator electrode 290 is mounted on exterior surface 275 as a substantially separate component from dilator exterior surface 275.

In examples, dilator 226, 272, 284 includes an anti-rotation feature configured to limit and/or eliminate rotation of dilator 226, 272, 284 caused by a force on dilator 226, 272, 284 acting in the proximal direction P. The anti-rotation feature may be configured to limit and/or eliminate rotation due to a force exerted on dilator 226, 272, 284 by inner member 230 due to an elasticity of inner member 230 (e.g., when inner member 230 stretches such that D2 is greater than D1 (FIGS. 3, 4)). The anti-rotation feature may be configured such that a torque on dilator 226, 272, 284 necessary to cause dilator 226, 272, 284 to move in a first direction (e.g., the proximal direction P) within tissue 217 (FIG. 4) is greater than a torque on dilator 226, 272, 284 necessary to cause dilator 226, 272, 284 to move in a second direction opposite the first direction (e.g., the distal direction D) within tissue 217 (FIG. 4). The anti-rotation feature may be, for example, a ramp formed on some portion of dilator exterior surface 250. The ramp may be configured to cause a first resistance to movement caused by the torque in the first direction and a second resistance to movement cause by the torque in the second direction, with the first resistance greater than the second resistance. In some examples, inner member 230 has a greater torsional strength when delivering the torque in the first direction to dilator 226, 272, 284 than when delivering the torque in the second direction to dilator 226, 272, 284.

Returning to FIG. 5, dilator 226 is configured to allow passage of probe wire 232 through at least some portion of dilator 226. For example, dilator 226 may define an inner lumen 260 and an inner lumen opening 261, with inner lumen 260 and inner lumen opening 261 sized to allow at least some portion of probe wire 232 (e.g., probe distal portion 246 (FIG. 3)) to pass therethrough. Inner lumen 260 may substantially extend from dilator proximal end 258 to dilator distal end 244. Inner lumen opening 261 may be substantially located at dilator distal end 244. In examples, inner lumen 260 substantially surrounds dilator axis D. Inner lumen 260 and inner lumen opening 261 are configured to allow slidable translation of at least probe distal portion 246 and probe electrode 234 through inner lumen 260 and inner lumen opening 261, such that an extension of probe electrode 234 distal to dilator distal end may be varied as a result of a pushing force (e.g., in the distal direction D) or a pulling force (e.g., in the proximal direction P) applied to probe wire 232.

As discussed, dilator 226 is depicted in FIG. 5 as a longitudinal cross-section with a cutting plane parallel to the page. Dilator 226 may have any longitudinal cross-section sufficient to convert a rotation about longitudinal axis L into a lateral translation of dilator 226 substantially parallel to longitudinal axis L. Further, dilator 226 may have any axial cross-section sufficient to engage a surrounding material 259 (FIG. 6). The axial cross-section of dilator 226 may be circular, oval shaped, polygonal, and may include straight and curved segments. The axial cross-section of dilator 226 may be substantially solid over substantially all or a portion of the axial cross-section, and may define open areas.

In some examples, dilator 226 includes a plug 251. In examples, plug 251 is configured to extend into inner lumen 260 to restrict and/or block a flow of fluid through inner lumen 260 (e.g., from lumen opening 261). Probe wire 232 may be configured to puncture and pass through plug 251 when probe wire 232 extends through inner lumen 260. In examples, plug 251 may comprise an expandable material (e.g., silicone) configured to substantially expand against a periphery of probe wire 232 when probe wire 232 passes through plug 251. In examples, plug 251 is configured to expand and substantially block inner lumen 260 when probe wire 232 is proximally withdrawn from inner lumen 260 and/or plug 251. In some examples, plug 251 comprises a material configured to swell when in contact with a fluid (e.g., water). In some examples, plug 251 is configured to release a therapeutic agent such as a steroid when in contact with a fluid within a patient.

Inner member 230 is configured to transmit a torque to dilator 226 and cause dilator 226 to rotate about dilator axis D and/or longitudinal axis L. Inner member 230 is configured to rotate (e.g., about longitudinal axis L) within lead body lumen 238 and relative lead interior surface 236. Additionally, at least some portion of inner member 230 may be configured to axially translate (e.g., substantially parallel to longitudinal axis L) relative to lead interior surface 236. For example, some portion of inner member 230 (e.g., point P2 (FIG. 2)) may be configured to axially translate within lead body lumen 238 when inner member 230 stretches as dilator 226 axially translates in the distal direction D. Inner member 230 may extend from dilator 226 through lead body lumen 238 and through an opening (not shown) proximal to lead body distal portion 220, such that a torque may be imparted on inner member 230 from a location outside of lead body distal portion 220. Inner member 230 may be configured to transmit the exerted torque through implantable medical lead 212 to dilator 226, in order to effect a rotation of dilator 226 relative to lead interior surface 236. In examples, inner member 230 is configured such that a clearance C is present between some portion of inner member 230 and lead interior surface 236 to assist in the independent rotation and translation of inner member 230 relative to lead interior surface 236, although this is not required. Inner member 230 may be configured to contact (intentionally or incidentally) lead interior surface 236 over some portion of or substantially all of inner member 230.

Inner member 230 may be configured to allow passage of probe wire 232 through at least some portion of inner member 230. For example, inner member 230 may define a channel 262 ("Inner member channel 262") sized to allow at least some portion of probe wire 232 (e.g., probe distal portion 246 (FIG. 3)) to pass therethrough. Inner member channel 262 may substantially extend from a distal end 263 of inner member 230 ("inner member distal end 263"). In examples, inner member channel 262 substantially surrounds at least some portion of longitudinal axis L. Inner member channel 262 may be configured to allow slidable translation of at least probe distal portion 246 and probe electrode 234 through inner member channel 262, such that probe distal portion 246 and probe electrode 234 may laterally translate as a result of a pushing force (e.g., in the distal direction D) or a pulling force (e.g., in the proximal direction P) applied to probe wire 232. In an example, inner member channel 262 opens to inner lumen 260 at inner member distal end 263, such that at least probe distal portion 246 and probe electrode 234 may pass from inner member channel 206 into inner lumen 260 of dilator 226.

Inner member 230 may be mechanically connected to dilator 226 in any manner which establishes a rotational coupling between inner member 230 and dilator 226. For example, inner member distal end 263 may be attached to dilator proximal end 258 by welding, soldering, adhesives, pins, or some other suitable fastening method. In some examples, inner member 230 is a torque coil having the form of a helix substantially surrounding a helix interior, and inner member 230 is configured such that, when inner member 230 is rotationally coupled to dilator 226, longitudinal axis L passes through at least some portion of the helix interior. Inner member 230 may define a helix substantially symmetric around some portion of longitudinal axis L. In some examples, the helix interior defines at least part of inner member channel 262.

In examples, implantable medical lead 212 includes a conductor (not shown) electrically connected to dilator electrode 227. In some examples, the conductor extends at least partially through inner member channel 262. In other examples, inner member 230 includes the conductor. For example, inner member 230 be an insulated, coiled conductor electrically connected to dilator electrode 227 and configured to transmit a torque to dilator 226. The insulated, coiled conductor may include one or more portions configured to translate (e.g., substantially parallel to longitudinal axis L) relative to lead interior surface 236. For example, some portion of the insulated, coiled conductor (e.g., point P2 (FIG. 2)) may be configured to stretch as dilator 226 axially translates in the distal direction D. The conductor of implantable medical lead 212 may be electrically connected to processing circuitry (e.g., IMD 128) configured to deliver electrical therapy and/or conduct electrical sensing via dilator electrode 227. IMD 128 may be configured to provide electrical signals, e.g., pacing therapy, through the conductor to dilator electrode 227, distal electrode 243, and/or return electrode 242, and receive electrical signals, e.g., sensed cardiac electrical signals, through the conductor from dilator electrode 227, distal electrode 243, and/or return electrode 242. In some examples, the conductor is configured to rotate when inner member 230 rotates. In other examples, the conductor is configured such that inner member 230 rotates relative to the conductor.

As discussed, inner member 230 is depicted in FIG. 5 as a longitudinal cross-section with a cutting plane parallel to the page. Inner member 230 may have any longitudinal cross-section sufficient to generate the rotational coupling with dilator 226. Further, inner member 230 may have any axial cross-section (e.g., a cross-section perpendicular to the longitudinal cross-section) sufficient to generate the rotational coupling with dilator 226. The axial cross-section may be circular, oval shaped, polygonal, and may include straight and curved segments. The axial cross-section may be substantially solid over substantially all or a portion of the axial cross-section, and may define open areas (e.g., a cross-section of inner member channel 262) over a portion of the axial cross-section.

As depicted in FIG. 5, implantable medical lead 212 includes one or more tines such as tine 224 attached to lead distal end 241 of lead body 218. Tine 224 is configured to penetrate tissues (e.g., tissue 217 (FIGS. 2, 3, 4)) when lead distal end 241 is in contact with or substantially adjacent to a tissue wall (e.g., tissue wall 215 (FIGS. 2, 3, 4)). In examples, tine 224 is an elongated member including fixed end 223 attached to lead body 218 and free end opposite fixed end 223. Tine 224 may be resiliently biased such that, unless sufficiently constrained (e.g., by delivery catheter 213 (FIGS. 2, 3)), tine 224 tends to assume a position where free end 225 has a greater radial displacement from longitudinal axis L than fixed end 223. In an example, the resilient biasing of tine 224 results in a tendency of free end 225 to return or attempt to return to an initial position relative to a point P on lead interior surface 236 when free end 225 is displaced from the initial position by, for example, a force F1 or force F2 acting on free end 225 in the direction shown in FIG. 5. The biasing tending to drive free end 225 radially outward when tine 224 is unconstrained may cause tine 224 to more securely anchor to the tissue of a patient. The one or more tines further include tine 266, which may be configured similarly to tine 224.

Figure 7:
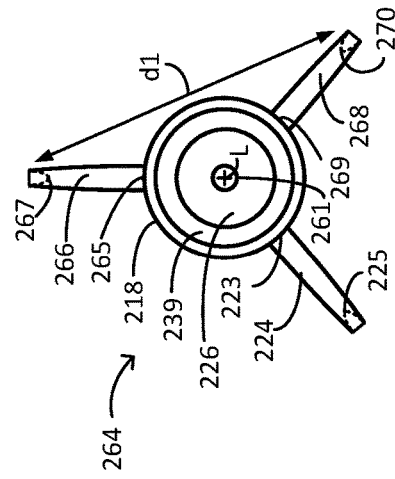
FIG. 7 is a plan view illustrating a plurality of tines.

In some examples, the one or more tines is a plurality of tines with each tine including a fixed end attached to lead body 218 and including a free end opposite the fixed end. For example, FIG. 7 illustrates an end view of implantable medical lead 212 with a plurality of tines 264 including tine 224, tine 266, and tine 268. Dilator 226, inner lumen opening 261, and longitudinal axis L are additionally depicted for reference. Dilator axis D (not shown) may be substantially coincident with longitudinal axis L. Tine 266 includes fixed end 265 attached to lead body 218 and free end 267 opposite fixed end 265. Tine 268 includes fixed end 269 attached to lead body 218 and free end 270 opposite fixed end 269. Free ends 225, 267, 270 are depicted in hidden lines. Each of fixed ends 223, 265, and 269 are attached to lead body 218 substantially at or adjacent to lumen opening 239 at lead body distal end 241. As illustrated, in examples, the one or more tines 224, 266, 268 may be configured such that a plurality of fixed ends 223, 265, 269 substantially surround lumen opening 239.

Individual tines within plurality of tines 264 may be spaced apart from each other around lumen opening 239. For example, FIG. 7 illustrates tines 266 and tine 268 spaced apart from each other by a distance d1. Distance d1 may expressed as a linear distance over a line oriented perpendicular to longitudinal axis L, and may be between any portion of tine 266 and any portion of tine 268 (e.g., may be between fixed end 265 and fixed end 269, between free end 267 and free and 270, or between other portions of tine 266 and tine 268). The distance d1 may also be expressed as an angle having a vertex on longitudinal axis L. In some examples, distance d1 may be in the range of 30 to 180 degrees. The illustrated number and arrangement of plurality of tines 264 is one non-limiting example, and implantable medical lead 212 may, in other examples, include a different number of individual tines comprising plurality of tines 264 and/or a different positions of one or more individual tines comprising plurality of tines 264. In an example, implantable medical lead 212 may include a plurality of tines 264 substantially equally distributed circumferentially around lumen opening 239.

One or more of tines 224, 266, 268 may be a substantially elastic member (e.g., may tend to return to a zero-stress shape in the absence of externally imparted forces), and may be configured to pierce and potentially penetrate into or through target tissue. One or more of tines 224, 266, 268 may be formed to have a preset shape and may be formed using any suitable material. In examples, one or more of tines 224, 266, 268 comprise a nickel-titanium alloy such as Nitinol.

Distal electrode 243, return electrode 242, dilator electrode 227, and/or probe electrode 234 may be configured to deliver low-voltage electrical pulses to the heart or may sense a cardiac electrical activity, e.g., depolarization and repolarization of the heart. Distal electrode 243, return electrode 242, dilator electrode 227, and/or probe electrode 234 may be any of a number of different types of electrodes, including ring electrodes, short coil electrodes, paddle electrodes, hemispherical electrodes, directional electrodes, or the like. Distal electrode 243, return electrode 242, dilator electrode 227, and/or probe electrode 234 may be the same or different types of electrodes. Each of distal electrode 243, return electrode 242, dilator electrode 227, and/or probe electrode 234 may be electrically isolated from any other of the distal electrode 243, return electrode 242, dilator electrode 227, and/or probe electrode 234 by an electrically insulating material between each electrode and any other electrode. Each of distal electrode 243, return electrode 242, dilator electrode 227, and/or probe electrode 234 may have its own separate conductor such that a voltage may be applied to or a signal sensed from the each electrode independently from the any other electrode. In some configurations, distal electrode 243, return electrode 242, dilator electrode 227, and/or probe electrode 234 may be coupled to a common conductor such that each electrode may apply a voltage simultaneously.

Figure 10:
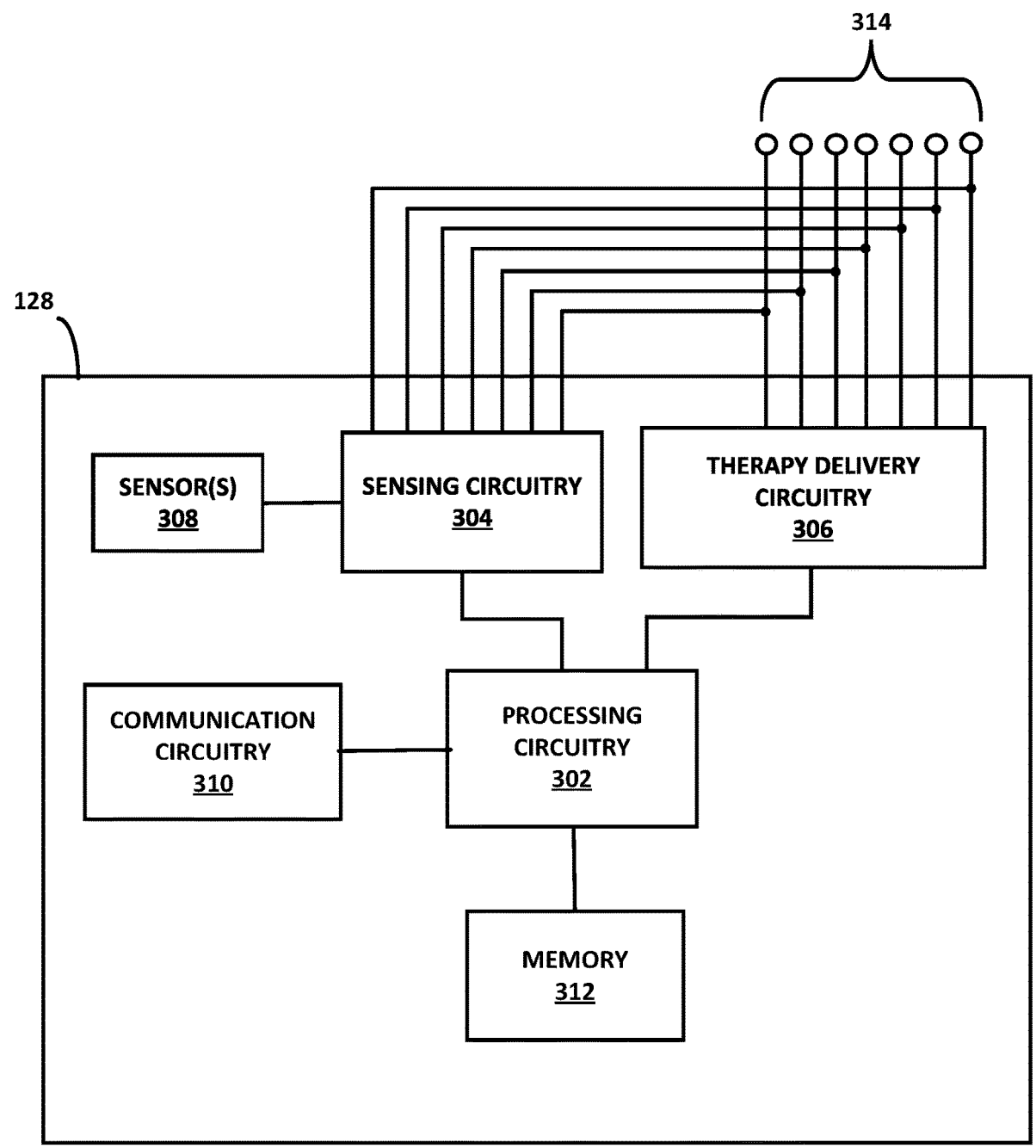
FIG. 10 is a schematic illustration of the circuitry of an IMD.

FIG. 10 is a functional block diagram illustrating an example configuration of IMD 128. As shown in FIG. 7, IMD 128 includes processing circuitry 302, sensing circuitry 304, therapy delivery circuitry 306, sensors 308, communication circuitry 310, and memory 312. In some examples, memory 312 includes computer-readable instructions that, when executed by processing circuitry 302, cause IMD 128 and processing circuitry 302 to perform various functions attributed to IMD 128 and processing circuitry 302 herein. Memory 312 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 302 may include fixed function circuitry and/or programmable processing circuitry. Processing circuitry 302 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 302 may include multiple components, such as any combination of one or more microprocessors, one or more controllers, one or more DSPs, one or more ASICs, or one or more FPGAs, as well as other discrete or integrated logic circuitry. The functions attributed to processing circuitry 302 herein may be embodied as software, firmware, hardware or any combination thereof.

In some examples, processing circuitry 302 may receive (e.g., from an external device), via communication circuitry 310, a respective value for each of a plurality of cardiac sensing parameters, cardiac therapy parameters (e.g., cardiac pacing parameters), and/or electrode vectors. Processing circuitry 302 may store such parameters and/or electrode vectors in memory 312.

Therapy delivery circuitry 306 and sensing circuitry 304 are electrically coupled to electrodes 314, which may correspond to distal electrode 243, return electrode 242, and/or dilator electrode 227, 282, 290 (FIGS. 2, 3, 4, 5, 6, 8, 9). Processing circuitry 302 is configured to control therapy delivery circuitry 306 to generate and deliver electrical therapy to heart 122 via electrodes 314. Electrical therapy may include, for example, pacing pulses, or any other suitable electrical stimulation. Processing circuitry 302 may control therapy delivery circuitry 306 to deliver electrical stimulation therapy via electrodes 314 according to one or more therapy parameter values, which may be stored in memory 312. Therapy delivery circuitry 306 may include capacitors, current sources, and/or regulators, in some examples.

In addition, processing circuitry 302 is configured to control sensing circuitry 304 to monitor signals from electrodes 314 in order to monitor electrical activity of heart 122. Sensing circuitry 304 may include circuits that acquire electrical signals, such as filters, amplifiers, and analog-to-digital circuitry. Electrical signals acquired by sensing circuitry 304 may include intrinsic and/or paced cardiac electrical activity, such as atrial depolarizations and/or ventricular depolarizations. Sensing circuitry 304 may filter, amplify, and digitize the acquired electrical signals to generate raw digital data. Processing circuitry 302 may receive the digitized data generated by sensing circuitry 304. In some examples, processing circuitry 302 may perform various digital signal processing operations on the raw data, such as digital filtering. In some examples, in addition to sensing circuitry 304, IMD 128 optionally may include sensors 308, which may be one or more pressure sensors and/or one or more accelerometers, as examples. Communication circuitry 310 may include any suitable hardware (e.g., an antenna), firmware, software, or any combination thereof for communicating with another device, e.g., external to the patient.

Figure 11:
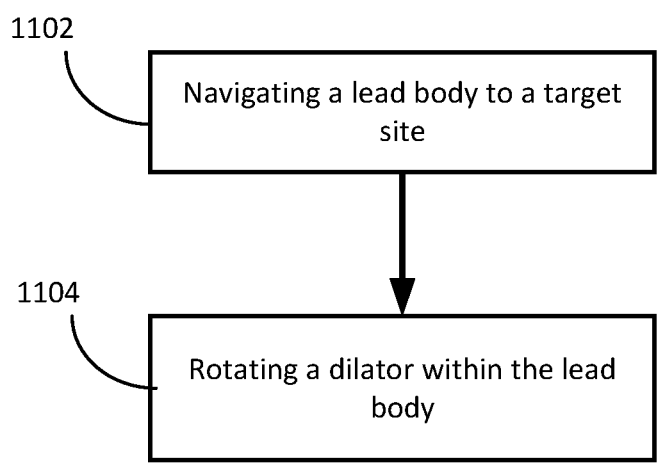
FIG. 11 illustrates an example technique for implanting a dilator electrode.

A technique for inserting a dilator 226 into the tissue at or near a target site 214 is illustrated in FIG. 11. Although the technique is described mainly with reference to implantable medical lead 212 of FIGS. 2, 3, 4, and 5, the technique may be applied to other implantable medical leads in other examples.

The technique includes navigating a lead body 218 to the target site 214 in a patient 116 (FIG. 1) (1102). Target site 214 may be location on a septal wall, such as an interventricular septal wall of a right ventricle (RV) of heart 122 (FIG. 1). The technique may include navigating a delivery catheter 213 to target site 214, and navigating a probe wire 232 to target site 214 using delivery catheter 213. The technique may include translating probe wire 232 and a probe electrode 234 through an inner lumen 260 and inner lumen opening 261 at a dilator distal end 244 of a dilator 226 within lead body 218. Probe wire 232 may penetrate a tissue wall 215 of tissue 217. The technique may include varying a penetration depth of probe wire 232 in tissues 217 to vary a location of a probe electrode 234 in tissue 217. The technique may include repositioning delivery catheter 213 to vary a penetration trajectory of probe wire 232. The technique may include delivering electrical therapy and/or conducting electrical sensing via probe electrode 234 (e.g., pace mapping) using processing circuitry in electrical communication with probe electrode 234.

The technique may include extending probe wire 232 and probe electrode 234 through tissue wall 217 and allowing at least a probe distal portion 246 to form a curvature such as loop 248. The technique may include forming loop 248 after pace mapping using probe electrode 234. Probe distal portion 246 may form the curvature such that loop 248 is in contact with or substantially adjacent to a tissue wall of tissue 217 opposite tissue wall 215. For example, probe distal portion 246 may form loop 248 in contact with or substantially adjacent to an endocardial surface of the interventricular septal wall of a left ventricle (LV) of heart 122 (FIG. 1). In examples, the technique includes imaging probe distal portion 246 using fluoroscopy or other imaging techniques.

The technique may include navigating lead body 218 over probe wire 232 to target site 214. Lead body 218 may be navigated to target site 214 within delivery catheter 213. Delivery catheter 213 may constrain one or more tines 224, 266, 268 extending from lead body 218 in a delivery configuration. The technique includes contacting the one or more tines 224, 266, 268 with tissue wall 215 at target site 214. Contacting the one or more tines 224, 266, 268 may include translating lead body 188 within delivery catheter 213 toward tissue wall 215. The technique includes grasping tissue wall 215 using one or more of tines 224, 266, 268. In examples, tines 224, 266, 268 are resiliently biased to expand radially outward from a longitudinal axis L of lead body 218 unless a free end 225, 267, 270 is constrained (e.g., by delivery catheter 213). Grasping the tissue wall may include withdrawing delivery catheter 213 and causing free end 225, 267, 270 to expand radially outward. The technique may include positioning a distal electrode 243 in close proximity or contact with tissue wall 215. The technique may include delivering electrical therapy and/or conducting electrical sensing via distal electrode 243 using processing circuitry (e.g., 1 MB 128 (FIG. 1)) in electrical communication with distal electrode 243.

The technique includes rotating dilator 226 within a lead body lumen 238 defined by a lead interior surface 236 of lead body 218 (1104). In examples, the technique includes translating dilator 226 within lead body lumen 238 toward tissue wall 215. The technique may include rotating dilator 226 around a dilator axis D (FIG. 8, 9). Rotating dilator 226 includes rotating an inner member 230 relative to lead interior surface 236 and causing a rotation of dilator 226 relative to lead interior surface 236. The technique includes translating dilator 226 into tissues 217 using the rotation of inner member 230. In examples, the technique includes engaging tissue wall 215 and/or tissue 217 with a set of helical threads 256 on a dilator exterior surface 250 of dilator 226 and converting the rotation of dilator 226 into a translation of dilator 226 substantially parallel to dilator axis D. In examples, the technique includes positioning a dilator electrode 227 within tissues 217 using the rotation of dilator 226. Positioning dilator electrode 227 may include placing dilator electrode 227 in electrical contact with tissues 217. The technique may include delivering electrical therapy and/or conducting electrical sensing via dilator electrode 227 using processing circuitry (e.g., 1 MB 128 (FIG. 1)) in electrical communication with dilator electrode 227.

The technique may include causing inner member 230 to stretch longitudinally as dilator 226 translates into tissues 217. Stretching inner member 230 may include increasing a displacement along longitudinal axis L between a first point P1 on inner member 230 and a second point P2 on inner member 230. Some portion of or substantially all of inner member 230 may be a helical coil substantially surrounding longitudinal axis L, and stretching inner member 230 may include causing the helical coil to stretch lengthwise along the longitudinal axis. The technique may include measuring electrical parameters while translating dilator 226 into tissue 217 and positioning dilator 226 within tissues 217 based on the pace mapping conducted using probe wire 232 and a probe electrode 234.

The technique may include withdrawing probe distal portion 246 from tissue wall 217. Withdrawing probe distal portion 246 may include withdrawing probe wire 232 proximally through inner lumen opening 261 and inner lumen 260 of dilator 226. Withdrawing probe wire 232 may include withdrawing probe wire 232 proximally through an inner member channel 262 defined by inner member 230.

The technique may include delivering electrical therapy and/or conducting electrical sensing via dilator electrode 227, distal electrode 243, and or return electrode 242 using processing circuitry (e.g., IMD 128 (FIG. 1)) in electrical communication with at least dilator electrode 227 and distal electrode 243. Implantable medical lead 212 may be configured to deliver a first electrical signal via dilator electrode 227 and a second electrical signal via distal electrode 243 using the processing circuitry (e.g., IMD 128). The technique may include using dilator electrode 227 to deliver electrical therapy to and/or conduct electrical sensing of tissue 217 and using distal electrode 243 to deliver electrical therapy to and/or conduct electrical sensing of tissue wall 215. For example, the technique may include using dilator electrode 227 to deliver electrical therapy to and/or conduct electrical sensing of a interventricular septum of heart 122 (FIG. 1) to activate a left bundle branch (LBB) of heart 122 and using distal electrode 243 to deliver electrical therapy to and/or conduct electrical sensing of an interventricular septal wall of a right ventricle (RV) of heart 122 to activate a right bundle branch (RBB) of heart 122.

The disclosure includes the following examples.

Example 1: An implantable medical lead comprising: a lead body comprising an interior surface defining a lumen, wherein the lead body defines a longitudinal axis; an inner member within the lumen, wherein the inner member is configured to rotate about the longitudinal axis and rotate relative to the interior surface; a dilator coupled to the inner member, wherein: the dilator is configured to rotate relative to the interior surface, the inner member is configured to transmit a torque to the dilator when the inner member rotates around the longitudinal axis, the dilator is configured to penetrate tissue when the dilator receives the torque and the dilator contacts the tissue, and the dilator includes a dilator electrode configured to provide stimulation to the tissue when the dilator penetrates the tissue; and a fixation member attached to a distal end of the lead body, wherein the fixation member is configured to secure the distal end of the lead body to the tissue.

Example 2: The implantable medical lead of example 1, wherein the lead body defines a lumen opening to the lumen at the distal end of the lead body, wherein the lumen opening is sized to allow passage of the dilator and some portion of the inner member therethrough.

Example 3: The implantable medical lead of example 1 or example 2, wherein the dilator defines a dilator axis, and wherein the dilator includes a helical screw thread on an exterior surface of the dilator, wherein the helical screw thread is configured to cause the dilator to translate substantially parallel to the dilator axis when the inner member transmits the torque to the dilator and the helical screw thread contacts a heart tissue.

Example 4: The implantable medical lead of any of examples 1-3, wherein the dilator defines a dilator axis, and wherein the inner member is configured to stretch when the dilator translates substantially parallel to the dilator axis.

Example 5: The implantable medical lead of any of examples 1-4, wherein the inner member is a helical coil.

Example 6: The implantable medical lead of any of examples 1-5, wherein the dilator defines an inner lumen and an inner lumen opening at a distal end of the dilator, and further comprising a probe wire configured to extend through the inner lumen and the inner lumen opening.

Example 7: The implantable medical lead of any of examples 1-6, wherein the probe wire includes an insulated section and an uninsulated section, wherein the uninsulated section is configured to extend through the inner lumen opening.

Example 8: The implantable medical lead of any of examples 1-7, wherein the lead body defines a lumen opening to the lumen at the distal end of the lead body, and wherein the dilator is configured to rotate relative to the interior surface at least when the dilator is distal to the lumen opening.

Example 9: The implantable medical lead of any of examples 1-8, wherein the fixation member includes one or more tines, wherein an individual tine in the one or more tines comprises a fixed end attached to the distal end of the lead body and a free end opposite the fixed end, and wherein the individual tine is resiliently biased to pivot the free end radially outward from the longitudinal axis.

Example 10: The implantable medical lead of any of examples 1-9, wherein the fixation member includes one or more tines, wherein an individual tine in the one or more tines comprises a fixed end attached to the distal end of the lead body, a free end opposite the fixed end, and a midpoint between the fixed end and the free end, wherein the individual tine is resiliently biased to establish a configuration wherein the midpoint is distal to the free end and distal to the fixed end.

Example 11: The implantable medical lead of any of examples 1-10, wherein: the lead body defines a lumen opening to the lumen at the distal end of the lead body, the fixation member includes a plurality of tines, wherein each tine in the plurality of tines comprises a fixed end attached to the distal end of the lead body and a free end opposite the fixed end, such that the plurality of tines comprise a plurality of fixed ends, and the plurality of fixed ends surround the lumen opening.

Example 12: The implantable medical lead of any of examples 1-11, wherein the inner member comprises a conductor electrically connected to the dilator electrode.

Example 13: The implantable medical lead of any of examples 1-12, further comprising a return electrode mounted to the lead body.

Example 14: The implantable medical lead of example 13, further comprising a distal electrode mounted to the lead body, wherein the distal electrode is distal to the return electrode.

Example 15: The implantable medical lead of any of examples 1-14, wherein the dilator defines a dilator axis, and wherein the dilator is configured to translate substantially parallel to the dilator axis and relative to the interior surface.

Example 16: The implantable medical lead of any of examples 1-15, wherein the dilator defines a dilator axis, and wherein the dilator comprises an exterior surface substantially in the form of a prolate spheroid surrounding the dilator axis.

Example 17: The implantable medical lead of any of examples 1-16, further comprising a probe wire configured to extend through the inner lumen and the inner lumen opening, wherein the probe wire comprises a shape-memory alloy biased to cause a section of the probe wire to form a loop when the section of the probe wire is extended distally through the inner lumen opening.

Example 18: The implantable medical lead of any of examples 1-17, wherein the lumen defined by the interior surface surrounds the longitudinal axis defined by the lead body.

Example 19: The implantable medical lead of any of examples 1-18, further comprising: a distal electrode mounted to the lead body, wherein the distal electrode is configured to contact a septal wall of a heart; and a return electrode mounted to the lead body, wherein the return electrode is proximal to the distal electrode.

Example 20: The implantable medical lead of example 19, wherein the dilator electrode is configured to be positioned within a septum when the distal electrode contacts the septal wall of the heart.

Example 21: The implantable medical lead of any of examples 1-20, further comprising: an implantable medical device coupled to the dilator electrode; a return electrode mounted to the lead body and coupled to the implantable medical device, wherein the implantable medical device is configured to deliver an electrical signal to the dilator electrode using the dilator electrode and the return electrode.

Example 22: The implantable medical device of example 21, further comprising a distal electrode mounted to the lead body and distal to the return electrode, wherein the electrical signal is a first electrical signal and wherein the implantable medical device is configured to deliver a second electrical signal to the distal electrode using the distal electrode and the return.

Example 23: An implantable medical lead comprising: a lead body comprising an interior surface defining a lumen, wherein the lead body defines a longitudinal axis and a lumen opening to the lumen at a distal end of the lead body; an inner member within the lumen, wherein the inner member is configured to rotate around the longitudinal axis and rotate relative to the interior surface; a dilator coupled to the inner member, wherein: the lumen opening is sized to allow passage of the dilator and some portion of the inner member through the lumen opening; the dilator includes a dilator electrode, the dilator is configured to rotate relative to the interior surface, the inner member is configured to transmit a torque to the dilator when the inner member rotates around the longitudinal axis, and the inner member and the dilator define an inner lumen, wherein the dilator defines an inner lumen opening to the inner lumen; a probe wire configured to extend through the inner lumen and the inner lumen opening; and one or more tines attached to a distal end of the lead body.

Example 24: The implantable medical lead of example 23, further comprising: a distal electrode mounted to the lead body, wherein the distal electrode is configured to contact a septal wall of a heart; and a return electrode mounted to the lead body, wherein the return electrode is proximal to the distal electrode.

Example 25: The implantable medical lead of example 23 or example 24, further comprising: an implantable medical device coupled to the dilator electrode; a return electrode mounted to the lead body and coupled to the implantable medical device, wherein the implantable medical device is configured to deliver a first electrical signal to the dilator electrode using the dilator electrode and the return electrode; and a distal electrode mounted to the lead body and coupled to the implantable medical device, wherein the implantable medical device is configured to deliver a second electrical signal to the distal electrode using the distal electrode and the return electrode.

Example 26: The implantable medical lead of any of examples 23-25, wherein the dilator defines a dilator axis, and wherein the dilator includes a helical screw thread on an exterior surface of the dilator, wherein the helical screw thread is configured cause the dilator to translate substantially parallel to the dilator axis when the inner member transmits the torque to the dilator and the dilator contacts a heart tissue.

Example 27: The implantable medical lead of any of examples 23-26, wherein the inner member is configured to stretch when the dilator translates substantially parallel to the dilator axis.

Example 28: The implantable medical lead of any of examples 23-27, wherein the inner member is configured to rotate within the lumen relative to the interior surface.

Example 29: The implantable medical lead of any of examples 23-28, wherein an individual tine in the one or more tines comprises a fixed end attached to the distal end of the lead body and a free end opposite the fixed end, wherein the individual tine is resiliently biased to pivot the free end radially outward from the longitudinal axis.

Example 30: A method of delivering a dilator electrode to a target site in a patient, the method comprising: navigating a lead body to the target site; contacting one or more tines attached to a distal end of the lead body with tissues at or near the target site; grasping the tissues at or near the target site using the one or more tines; rotating an inner member within a lumen defined by an interior surface of the lead body relative to the interior surface; rotating a dilator including the dilator electrode using the rotation of the inner member; and translating the dilator into the tissues at or near the target site using the rotation of the dilator.

Example 31: The method of example 30 further comprising translating a probe wire through an inner lumen defined by the inner member and the dilator.

Example 32: The method of example 30 or example 31, further comprising penetrating the tissues at or near the target site with a distal end of the probe wire using the translation of the probe wire through the inner lumen.

Example 33: The method of example 31 or example 32, further comprising transmitting an electrical signal to the tissue at or near the target site using the probe wire.

Example 34: The method of any of examples 30-33, further comprising laterally translating the dilator from a first position proximal to a lumen opening to a second position distal to the lumen opening, wherein the lumen opening is defined by the lead body at a distal end of the lead body.

Example 35: The method of any of examples 30-34, further comprising rotating the inner member within the lumen relative to the interior surface.

Example 36: The method of any of examples 30-35 further comprising delivering an electrical signal to the dilator electrode using an implantable medical device electrically connected to the dilator electrode and electrically connected to a return electrode mounted to the lead body.

Example 37: The method of any of examples 30-36 further comprising delivering an electrical signal to a distal electrode mounted to the lead body using an implantable medical device electrically connected to the distal electrode and electrically connected to a return electrode mounted to the lead body, wherein the distal electrode is distal to the return electrode.

Example 38: The method of any of examples 30-37 wherein contacting the one or more tines with the tissues at or near the target site comprises using a resilient biasing of the one or more tines to expand a free end of the one or more tines radially outward from a longitudinal axis defined by the lead body.

Various examples of the disclosure have been described. Any combination of the described systems, operations, or functions is contemplated. These and other examples are within the scope of the following claims.

What is claimed is:

1. An implantable medical lead comprising:
    a lead body comprising an interior surface defining a lumen and a lumen opening which opens to the lumen at a distal end of the lead body, wherein the lead body defines a longitudinal axis;
    an inner member within the lumen, wherein the inner member is configured to rotate about the longitudinal axis and rotate relative to the interior surface;
    a dilator coupled to the inner member, wherein:
        the dilator is configured to rotate relative to the interior surface,
        the dilator is configured to slidably translate within the lumen,
        the inner member is configured to transmit a torque to the dilator when the inner member rotates around the longitudinal axis,
        the dilator is configured to penetrate tissue when the dilator receives the torque and the dilator contacts the tissue,
        the dilator includes a dilator electrode configured to provide stimulation to the tissue when the dilator penetrates the tissue, and
        the dilator defines an inner lumen and an inner lumen opening at a distal end of the dilator;
    a probe wire including a probe distal portion configured to extend through the inner lumen, through the inner lumen opening, and distal to the lumen opening of the lead body, wherein the probe distal portion includes a probe electrode configured to electrically communicate with processing circuitry to electrically map a wall of a heart of a patient; and
    a fixation member attached to a distal end of the lead body, wherein the fixation member is configured to secure the distal end of the lead body to the tissue.

2. The implantable medical lead of claim 1, wherein the lumen opening is sized to allow passage of the dilator and some portion of the inner member therethrough.

3. The implantable medical lead of claim 1, wherein the dilator defines a dilator axis, and wherein the dilator includes a helical screw thread on an exterior surface of the dilator, wherein the helical screw thread is configured to cause the dilator to translate substantially parallel to the dilator axis when the inner member transmits the torque to the dilator and the helical screw thread contacts a heart tissue.

4. The implantable medical lead of claim 1, wherein the dilator defines a dilator axis, and wherein the inner member is configured to stretch when the dilator translates substantially parallel to the dilator axis.

5. The implantable medical lead of claim 1, wherein the probe wire comprises a shape-memory alloy biased to cause the probe distal portion to form a loop when the probe wire extends distally through the inner lumen opening.

6. The implantable medical lead of claim 1, wherein the fixation member includes one or more tines, wherein an individual tine in the one or more tines comprises a fixed end attached to the distal end of the lead body and a free end opposite the fixed end, and wherein the individual tine is resiliently biased to pivot the free end radially outward from the longitudinal axis.

7. The implantable medical lead of claim 1, wherein the inner member comprises a conductor electrically connected to the dilator electrode.

8. The implantable medical lead of claim 1, further comprising a return electrode mounted to the lead body, wherein the return electrode is configured to electrically communicate with the processing circuitry when the dilator electrode provides stimulation to the tissue.

9. The implantable medical lead of claim 1, further comprising a distal electrode mounted to the lead body, wherein the distal electrode is configured to provide stimulation to the tissue when the fixation members secure the distal end of the lead body to the tissue.

10. The implantable medical lead of claim 1, wherein the dilator defines a dilator axis, and wherein the dilator comprises an exterior surface substantially in the form of a prolate spheroid surrounding the dilator axis.

11. The implantable medical lead of claim 1, wherein the inner member defines a helical coil.

12. The implantable medical lead of claim 1, further comprising:
    an implantable medical device coupled to the dilator electrode; and
    a return electrode mounted to the lead body and coupled to the implantable medical device, wherein the implantable medical device is configured to deliver an electrical signal to the dilator electrode using the dilator electrode and the return electrode.

13. The implantable medical lead device of claim 12, further comprising a distal electrode mounted to the lead body and distal to the return electrode, wherein the electrical signal is a first electrical signal and wherein the implantable medical device is configured to deliver a second electrical signal to the distal electrode using the distal electrode and the return electrode.

14. The implantable medical lead of claim 1, wherein the probe distal portion is configured to extend through the inner lumen and the inner lumen opening such that the probe distal portion extends distal to a lumen opening at a distal end of the lead body, and further comprising the processing circuitry with which the probe electrode is configured to electrically communicate, the processing circuitry configured to:
    electrically communicate with the probe electrode when the probe distal portion extends distal to the lumen opening, and
    electrically map the wall of the heart using the electrical communication with the probe electrode; and
    electrically communicate with the dilator electrode to provide electrical stimulation therapy to the wall of the heart.

15. The implantable medical lead of claim 1, further comprising an anti-rotation feature supported by an exterior surface of the dilator,
    wherein the dilator is configured to laterally translate relative to the interior surface in a distal direction within the tissue when the inner member transmits the torque in a first direction and laterally translate relative to the interior surface in a proximal direction within the tissue when the inner member transmits the torque in a second direction, and wherein the anti-rotation is configured to cause a first resistance to movement of the dilator in the proximal direction and a second resistance to movement of the dilator in the distal direction, wherein the first resistance is greater than the second resistance.

16. The implantable medical lead of claim 1, wherein the dilator is configured to translate within the lumen from a first position proximal to the distal end of the lead body to a second position distal to the distal end of the lead body, and wherein the inner member is configured to translate relative to the inner surface when the dilator translates from the first position to the second position.

17. An implantable medical lead comprising:
a lead body comprising an interior surface defining a lumen, wherein the lead body defines a longitudinal axis and a lumen opening to the lumen at a distal end of the lead body;
an inner member within the lumen, wherein the inner member is configured to rotate around the longitudinal axis and rotate relative to the interior surface;
a dilator coupled to the inner member, wherein:
the dilator is configured to slidably translate within the lumen,
the lumen opening is sized to allow passage of the dilator and some portion of the inner member through the lumen opening,
the dilator includes a dilator electrode configured to electrically communicate with processing circuitry to deliver electrical stimulation therapy to a wall of a heart,
the dilator is configured to rotate relative to the interior surface when the inner member rotates relative to the interior surface,
the inner member is configured to transmit a torque to the dilator when the inner member rotates around the longitudinal axis,
the inner member and the dilator define an inner lumen, and
the dilator defines an inner lumen opening to the inner lumen; and
a probe wire including a probe distal portion configured to extend through the inner lumen and the inner lumen opening, wherein the probe distal portion includes a probe electrode, wherein the probe wire is configured to slidably translate within the inner lumen, and wherein the probe electrode is configured to electrically communicate with the processing circuitry to electrically map the wall of the heart; and one or more tines attached to a distal end of the lead body.

18. The implantable medical lead of claim 17, wherein the dilator defines a dilator axis, and wherein the dilator includes a helical screw thread on an exterior surface of the dilator, wherein the helical screw thread is configured cause the dilator to translate substantially parallel to the dilator axis when the inner member transmits the torque to the dilator and the dilator contacts a heart tissue.

19. A method of delivering a dilator electrode to a target site in a patient, the method comprising:
navigating an implantable medical lead to the target site, wherein the implantable medical lead includes:
a lead body comprising an interior surface defining a lumen and defining a lumen opening which opens to the lumen at a distal end of the lead body, wherein the lead body defines a longitudinal axis,
an inner member within the lumen, and
a dilator coupled to the inner member, wherein the inner member is configured to rotate about the longitudinal axis and rotate relative to the interior surface to transmit a torque to the dilator, wherein the dilator is configured to rotate relative to the interior surface and configured to slidably translate within the lumen, wherein the dilator is configured to penetrate tissue when the dilator receives the torque and the dilator contacts the tissue, and wherein the dilator includes a dilator electrode configured to provide stimulation to the tissue when the dilator penetrates the tissue; securing the distal end of the lead body to the wall of the heart using a fixation member attached to the distal end of the lead body;
extending a probe distal portion of a probe wire through an inner lumen of the dilator and through an inner lumen opening defined by a distal portion of the dilator to extend the probe distal portion distal to a lumen opening at a distal end of the lead body, wherein the probe distal portion includes a probe electrode, the probe electrode configured to electrically communicate with processing circuitry to electrically map a wall of a heart of the patient;
rotating the inner member relative to the interior surface;
rotating the dilator using the rotation of the inner member; and
penetrating the tissue with the dilator using the rotation of the dilator.

20. The method of claim 19, further comprising:
electrically communicating, using the probe electrode, with the processing circuitry; and
electrically communicating, using the dilator electrode, with the processing circuitry.

* * * * *